(12) United States Patent
Demetriou et al.

(10) Patent No.: US 8,277,495 B2
(45) Date of Patent: Oct. 2, 2012

(54) METHOD AND APPARATUS FOR TREATING A DISEASED NAIL

(75) Inventors: Constantinos Demetriou, Nicosia (CY); James C. Hsia, Weston, MA (US)

(73) Assignee: Candela Corporation, Wayland, MA (US)

( * ) Notice: Subject to any disclaimer, the term of this patent is extended or adjusted under 35 U.S.C. 154(b) by 1575 days.

(21) Appl. No.: 11/229,024

(22) Filed: Sep. 16, 2005

(65) Prior Publication Data

US 2006/0212098 A1 Sep. 21, 2006

Related U.S. Application Data

(60) Provisional application No. 60/644,245, filed on Jan. 13, 2005, provisional application No. 60/656,356, filed on Feb. 25, 2005.

(51) Int. Cl.
*A61B 5/06* (2006.01)

(52) U.S. Cl. ............. 607/88; 607/96; 607/101; 128/898

(58) Field of Classification Search ............ 606/3, 8–12, 606/20–26; 607/88–91, 93, 96–102, 108, 607/111; 128/898
See application file for complete search history.

(56) References Cited

U.S. PATENT DOCUMENTS

| | | |
|---|---|---|
| 3,404,350 A | 10/1968 | Muncheryan |
| 3,538,919 A | 11/1970 | Meyer et al. |
| 3,693,623 A | 9/1972 | Harte et al. |
| 3,769,963 A | 11/1973 | Goldman et al. |
| 3,834,391 A | 9/1974 | Block |
| 3,900,034 A | 8/1975 | Katz et al. |
| 3,916,143 A | 10/1975 | Farrell |
| 4,388,924 A | 6/1983 | Weissman et al. |
| 4,461,294 A | 7/1984 | Baron |
| 4,608,978 A | 9/1986 | Rohr |
| 4,617,926 A | 10/1986 | Sutton |
| 4,733,660 A | 3/1988 | Itzkan |
| 4,819,669 A | 4/1989 | Politzer |
| 4,846,179 A | 7/1989 | O'Connor |
| 4,854,320 A | 8/1989 | Dew et al. |
| 4,905,690 A | 3/1990 | Ohshiro et al. |
| 4,930,504 A | 6/1990 | Diamantopoulos et al. |
| 4,976,709 A | 12/1990 | Sand |
| 4,985,027 A | 1/1991 | Dressel |

(Continued)

FOREIGN PATENT DOCUMENTS

CA 1041610 10/1978

(Continued)

OTHER PUBLICATIONS

Bartley et al., "An Experimental Study to Compare Methods of Eyelash Ablation," Ophthalmology 94: 1286-1289 (1987).

(Continued)

*Primary Examiner* — Ahmed Farah
(74) *Attorney, Agent, or Firm* — Proskauer Rose LLP

(57) ABSTRACT

The invention generally relates to treating diseased nails, and more particularly to treating diseased nails using radiation and/or another form of energy to substantially deactivate the source of the disease. A nail treatment can be performed by a medical professional without the use of a dying agent or an exogenous chromophore, and the treatment can be effective at eliminating the source of the disease without subjecting a patient to adverse side effects or causing substantial unwanted injury to surrounding tissue.

39 Claims, 8 Drawing Sheets

U.S. PATENT DOCUMENTS

| | | | |
|---|---|---|---|
| 5,000,752 A | 3/1991 | Hoskin et al. |
| 5,002,051 A | 3/1991 | Dew et al. |
| 5,019,034 A | 5/1991 | Weaver et al. |
| 5,050,597 A | 9/1991 | Daikuzono |
| 5,057,104 A | 10/1991 | Chess |
| 5,059,192 A | 10/1991 | Zaias |
| 5,102,410 A | 4/1992 | Dressel |
| 5,112,328 A | 5/1992 | Tabaoda et al. |
| 5,133,708 A | 7/1992 | Smith |
| 5,137,530 A | 8/1992 | Sand |
| 5,139,495 A | 8/1992 | Daikuzono |
| 5,140,984 A | 8/1992 | Dew et al. |
| 5,143,063 A | 9/1992 | Fellner |
| 5,151,098 A | 9/1992 | Loertscher |
| 5,165,418 A | 11/1992 | Tankovich |
| 5,182,857 A | 2/1993 | Simon |
| 5,190,032 A | 3/1993 | Zacoi |
| 5,226,907 A | 7/1993 | Tankovich |
| 5,282,797 A | 2/1994 | Chess |
| 5,290,273 A | 3/1994 | Tan |
| 5,304,169 A | 4/1994 | Sand |
| 5,304,170 A | 4/1994 | Green |
| 5,312,395 A | 5/1994 | Tan et al. |
| 5,320,618 A | 6/1994 | Gustafsson |
| 5,334,190 A | 8/1994 | Seiler |
| 5,336,217 A | 8/1994 | Buys et al. |
| 5,344,418 A | 9/1994 | Ghaffari |
| 5,348,551 A | 9/1994 | Spears et al. |
| 5,360,425 A | 11/1994 | Cho |
| 5,374,265 A | 12/1994 | Sand |
| 5,394,492 A | 2/1995 | Hwang |
| 5,397,327 A | 3/1995 | Koop et al. |
| 5,405,368 A | 4/1995 | Eckhouse |
| 5,409,479 A | 4/1995 | Dew et al. |
| 5,423,803 A | 6/1995 | Tankovich et al. |
| 5,425,728 A | 6/1995 | Tankovich |
| 5,437,658 A | 8/1995 | Muller et al. |
| 5,445,146 A | 8/1995 | Bellinger |
| 5,445,634 A | 8/1995 | Keller |
| 5,454,840 A | 10/1995 | Krakovsky et al. |
| 5,464,436 A | 11/1995 | Smith |
| 5,464,610 A | 11/1995 | Hayes, Jr. et al. |
| 5,474,549 A | 12/1995 | Ortiz et al. |
| 5,484,432 A | 1/1996 | Sand |
| 5,486,172 A | 1/1996 | Chess |
| 5,522,813 A | 6/1996 | Trelles |
| 5,527,350 A | 6/1996 | Grove et al. |
| 5,569,242 A | 10/1996 | Lax et al. |
| 5,595,568 A | 1/1997 | Anderson et al. |
| 5,597,559 A | 1/1997 | Olejnik et al. |
| 5,606,798 A | 3/1997 | Kelman |
| 5,614,339 A | 3/1997 | Tankovich |
| 5,647,866 A | 7/1997 | Zaias et al. |
| 5,648,389 A | 7/1997 | Gans et al. |
| 5,653,706 A | 8/1997 | Zavislan et al. |
| 5,683,380 A | 11/1997 | Eckhouse et al. |
| 5,707,403 A | 1/1998 | Grove et al. |
| 5,713,845 A | 2/1998 | Tankovich |
| 5,735,844 A | 4/1998 | Anderson et al. |
| 5,746,736 A | 5/1998 | Tankovich |
| 5,752,948 A | 5/1998 | Tankovich et al. |
| 5,752,949 A | 5/1998 | Tankovich et al. |
| 5,755,753 A | 5/1998 | Knowlton |
| 5,807,385 A | 9/1998 | Keller |
| 5,810,801 A | 9/1998 | Anderson et al. |
| 5,814,040 A | 9/1998 | Nelson et al. |
| 5,817,089 A | 10/1998 | Tankovich et al. |
| 5,820,626 A | 10/1998 | Baumgardner |
| 5,840,283 A | 11/1998 | Sorenson et al. |
| 5,860,967 A | 1/1999 | Zavislan et al. |
| 5,868,732 A | 2/1999 | Waldman et al. |
| 5,871,480 A | 2/1999 | Tankovich |
| 5,897,549 A | 4/1999 | Tankovich |
| 5,925,035 A | 7/1999 | Tankovich |
| 5,925,178 A | 7/1999 | Martin et al. |
| 5,947,956 A | 9/1999 | Karell |
| 5,954,710 A | 9/1999 | Paolini et al. |
| 5,964,749 A | 10/1999 | Eckhouse et al. |
| 5,972,317 A | 10/1999 | Sorenson et al. |
| 5,979,454 A | 11/1999 | Anvari et al. |
| 5,997,530 A | 12/1999 | Nelson et al. |
| 6,030,378 A | 2/2000 | Stewart |
| 6,036,684 A | 3/2000 | Tankovich et al. |
| 6,050,990 A | 4/2000 | Tankovich et al. |
| 6,063,074 A | 5/2000 | Tankovich |
| 6,063,108 A | 5/2000 | Salansky et al. |
| 6,077,294 A | 6/2000 | Cho et al. |
| 6,083,217 A | 7/2000 | Tankovich |
| 6,090,788 A | 7/2000 | Lurie |
| 6,096,029 A | 8/2000 | O'Donnell, Jr. |
| 6,106,514 A | 8/2000 | O'Donnell, Jr. |
| 6,106,516 A | 8/2000 | Massengill |
| 6,120,497 A | 9/2000 | Anderson et al. |
| 6,120,519 A | 9/2000 | Weber et al. |
| 6,152,917 A | 11/2000 | Tankovich |
| 6,162,211 A | 12/2000 | Tankovich et al. |
| 6,168,590 B1 | 1/2001 | Neev |
| 6,171,301 B1 | 1/2001 | Nelson et al. |
| 6,183,773 B1 | 2/2001 | Anderson |
| 6,206,873 B1 | 3/2001 | Paolini et al. |
| 6,235,016 B1 | 5/2001 | Stewart |
| 6,248,103 B1 | 6/2001 | Tannenbaum et al. |
| 6,267,771 B1 | 7/2001 | Tankovich et al. |
| 6,273,884 B1 | 8/2001 | Altshuler et al. |
| 6,280,438 B1 | 8/2001 | Eckhouse et al. |
| 6,302,863 B1 | 10/2001 | Tankovich |
| 6,315,756 B1 | 11/2001 | Tankovich |
| 6,350,276 B1 | 2/2002 | Knowlton |
| 6,387,089 B1 | 5/2002 | Kreindel et al. |
| 6,403,063 B1 | 6/2002 | Sawyer |
| 6,405,090 B1 | 6/2002 | Knowlton |
| 6,408,212 B1 | 6/2002 | Neev |
| 6,416,749 B1 | 7/2002 | Hayes, Jr. et al. |
| 6,436,094 B1 | 8/2002 | Reuter |
| 6,436,127 B1 | 8/2002 | Anderson et al. |
| 6,511,475 B1 | 1/2003 | Altshuler et al. |
| 6,517,532 B1 | 2/2003 | Altshuler et al. |
| 6,530,920 B1 | 3/2003 | Whitcroft et al. |
| 6,562,054 B1 | 5/2003 | Weber et al. |
| 6,569,156 B1 | 5/2003 | Tankovich et al. |
| 6,600,951 B1 | 7/2003 | Anderson |
| 6,605,079 B2 | 8/2003 | Shanks et al. |
| 6,605,080 B1 | 8/2003 | Altshuler et al. |
| 6,613,040 B2 | 9/2003 | Tankovich et al. |
| 6,613,042 B1 | 9/2003 | Tankovich et al. |
| 6,632,219 B1 | 10/2003 | Baranov et al. |
| 6,648,904 B2 | 11/2003 | Altshuler et al. |
| 6,659,999 B1 | 12/2003 | Anderson et al. |
| 6,663,658 B1 | 12/2003 | Kollias et al. |
| 6,663,659 B2 | 12/2003 | McDaniel |
| 6,676,655 B2 | 1/2004 | McDaniel |
| 6,723,090 B2 | 4/2004 | Altshuler et al. |
| 6,733,492 B2 | 5/2004 | Ota et al. |
| 6,743,222 B2 | 6/2004 | Durkin et al. |
| 6,761,697 B2 | 7/2004 | Rubinstenn et al. |
| 6,776,790 B1 | 8/2004 | Maruyama et al. |
| 6,807,297 B1 | 10/2004 | Tankovich et al. |
| 6,902,563 B2 | 6/2005 | Wilkens et al. |
| 6,920,883 B2 | 7/2005 | Bessette et al. |
| 6,926,683 B1 | 8/2005 | Kochman et al. |
| 6,960,201 B2 | 11/2005 | Cumbie |
| 6,984,228 B2 | 1/2006 | Anderson et al. |
| 6,989,023 B2 | 1/2006 | Black |
| 6,997,923 B2 | 2/2006 | Anderson et al. |
| 7,020,528 B2 | 3/2006 | Neev |
| 7,033,381 B1 | 4/2006 | Larsen |
| 7,060,061 B2 | 6/2006 | Altshuler et al. |
| 7,090,670 B2 | 8/2006 | Sink |
| 7,118,563 B2 | 10/2006 | Weckwerth et al. |
| 7,137,979 B2 | 11/2006 | Conrad et al. |
| 7,184,614 B2 | 2/2007 | Slatkine |
| 7,220,254 B2 | 5/2007 | Altshuler et al. |
| 7,292,893 B2 | 11/2007 | Hoenig et al. |
| 7,306,620 B2 * | 12/2007 | Cumbie ............... 607/88 |
| 2002/0161357 A1 | 10/2002 | Anderson et al. |
| 2002/0169442 A1 | 11/2002 | Neev |
| 2002/0173780 A1 | 11/2002 | Altshuler et al. |

| | | | |
|---|---|---|---|
| 2002/0183789 A1 | 12/2002 | Neev | |
| 2003/0004499 A1* | 1/2003 | McDaniel | 606/3 |
| 2003/0032950 A1 | 2/2003 | Altshuler et al. | |
| 2003/0036749 A1 | 2/2003 | Durkin et al. | |
| 2003/0055413 A1* | 3/2003 | Altshuler et al. | 606/9 |
| 2003/0153962 A1 | 8/2003 | Cumbie | |
| 2003/0181847 A1 | 9/2003 | Bruno-Raimondi | |
| 2003/0216719 A1 | 11/2003 | Debenedictis et al. | |
| 2004/0005349 A1 | 1/2004 | Neev | |
| 2004/0036975 A1 | 2/2004 | Slatkine | |
| 2004/0039312 A1 | 2/2004 | Hillstead et al. | |
| 2004/0073079 A1 | 4/2004 | Altshuler et al. | |
| 2004/0093042 A1 | 5/2004 | Altshuler et al. | |
| 2004/0126272 A1 | 7/2004 | Bornstein | |
| 2004/0143247 A1 | 7/2004 | Anderson et al. | |
| 2004/0156743 A1 | 8/2004 | Bornstein | |
| 2004/0167499 A1 | 8/2004 | Grove et al. | |
| 2004/0167501 A1 | 8/2004 | Island et al. | |
| 2004/0167592 A1 | 8/2004 | Grove et al. | |
| 2004/0176754 A1 | 9/2004 | Island et al. | |
| 2004/0176823 A1 | 9/2004 | Island et al. | |
| 2004/0176824 A1 | 9/2004 | Weckwerth et al. | |
| 2004/0197280 A1 | 10/2004 | Repka | |
| 2004/0217675 A1 | 11/2004 | Desilets et al. | |
| 2004/0249426 A1 | 12/2004 | Hoenig et al. | |
| 2005/0038375 A1 | 2/2005 | Nitzan et al. | |
| 2005/0049582 A1 | 3/2005 | DeBenedictis et al. | |
| 2005/0055055 A1 | 3/2005 | Neev | |
| 2005/0085878 A1 | 4/2005 | Wilkens et al. | |
| 2005/0102009 A1 | 5/2005 | Costantino | |
| 2005/0131439 A1 | 6/2005 | Brett | |
| 2005/0137654 A1 | 6/2005 | Hoenig et al. | |
| 2005/0215987 A1 | 9/2005 | Slatkine | |
| 2005/0234527 A1 | 10/2005 | Slatkine | |
| 2005/0256515 A1 | 11/2005 | Anderson et al. | |
| 2006/0004306 A1 | 1/2006 | Altshuler et al. | |
| 2006/0004347 A1 | 1/2006 | Altshuler et al. | |
| 2006/0004425 A1 | 1/2006 | Cumbie | |
| 2006/0009749 A1 | 1/2006 | Weckwerth et al. | |
| 2006/0009750 A1 | 1/2006 | Altshuler et al. | |
| 2006/0013533 A1 | 1/2006 | Slatkine | |
| 2006/0020309 A1 | 1/2006 | Altshuler et al. | |
| 2006/0030908 A1 | 2/2006 | Powell et al. | |
| 2006/0074468 A1 | 4/2006 | Neev | |
| 2006/0079948 A1 | 4/2006 | Dawson | |
| 2006/0129214 A1 | 6/2006 | Da Silva et al. | |
| 2006/0142750 A1 | 6/2006 | Da Silva et al. | |
| 2006/0206173 A1* | 9/2006 | Gertner et al. | 607/88 |
| 2006/0224148 A1 | 10/2006 | Cho et al. | |
| 2006/0247609 A1 | 11/2006 | Mirkov et al. | |
| 2006/0253112 A1 | 11/2006 | Suarez et al. | |
| 2006/0259102 A1 | 11/2006 | Slatkine | |
| 2006/0265032 A1 | 11/2006 | Hennings et al. | |
| 2006/0293722 A1 | 12/2006 | Slatkine et al. | |
| 2008/0071334 A1* | 3/2008 | Hoenig et al. | 607/100 |

FOREIGN PATENT DOCUMENTS

| | | |
|---|---|---|
| CA | 2131750 | 1/1996 |
| DE | 195 12 481 | 10/1995 |
| DE | 19952045 | 8/2001 |
| EP | 0 142 671 | 5/1985 |
| EP | 0 292 621 | 11/1988 |
| EP | 0 348 862 | 1/1990 |
| EP | 0 575 274 | 12/1993 |
| EP | 0724866 A1 | 8/1996 |
| EP | 0763371 A2 | 3/1997 |
| GB | 2 123 287 | 2/1984 |
| GB | 2 336 545 | 10/1999 |
| JP | 63-249577 | 10/1988 |
| JP | 64-080309 | 3/1989 |
| JP | 03-193003 | 8/1991 |
| JP | 04-067860 | 3/1992 |
| JP | 04-322668 | 11/1992 |
| JP | 5-329218 | 12/1993 |
| WO | WO 84/02644 | 7/1984 |
| WO | WO 86/02783 | 5/1986 |
| WO | WO 89/00027 | 1/1989 |
| WO | WO 92/16338 | 10/1992 |
| WO | WO 92/19165 | 11/1992 |
| WO | WO 93/05920 | 4/1993 |
| WO | WO 95/15134 | 6/1995 |
| WO | WO 95/15725 | 6/1995 |
| WO | WO 97/37723 | 10/1997 |
| WO | WO 99/04628 | 2/1999 |
| WO | WO 99/27863 | 6/1999 |
| WO | WO 02/35983 | 5/2002 |
| WO | WO 02/053050 | 7/2002 |
| WO | WO 02/087700 | 11/2002 |
| WO | WO 03/005921 | 1/2003 |
| WO | WO 03/039478 | 5/2003 |
| WO | WO 03/068310 | 8/2003 |
| WO | WO 04/000150 | 12/2003 |
| WO | WO 2004/086947 | 10/2004 |
| WO | WO 2005/046793 | 5/2005 |

OTHER PUBLICATIONS

Berlien et al., "Lasers in Pediatric Surgery," Progress in Pediatric Surgery 25: 5-22 (1990).

Campbell, D.C., "Thermoablation Treatment for Trichiasis Using the Argon Laser," Australian and New Zealand Journal of Ophthalmology 18(4): 427-430 (1990).

Dixon et al., "Argon and Neodymium YAG Laser Therapy of Dark Nodular Port Wine Stains in Older Patients," Lasers in Surgery and Medicine 6: 5-11 (1986).

Dover et al., "Pigmented Guinea Pig Skin Irradiated With Q-Switched Ruby Laser Pulses," Arch. Dermatol. 125: 43-49 (1989).

Dover et al., "Illustrated Cutaneous Laser Surgery," in A Practioner's Guide, ed: Appleton & Lange, Norwalk, Connecticut (1990).

Dover et al., "Laser Hair Removal," 1-6.

Finkel et al., "Pulsed Alexandrite Laser Technology for Noninvasive Hair Removal," Journal of Clinical Laser Medicine & Surgery 15(5): 225-229 (1997).

Finkelstein et al., "Epilation of Hair-Bearing Urethral Grafts Using the Neodymium: YAG Surgical Laser," The Journal of Urology 146: 840-842 (1991).

Gilchrest et al., "Chilling Port Wine Stains Improves the Response to Argon Laser Therapy," Plastic and Reconstructive Surgery 69(2): 278-283 (1982).

Goldman et al., "Effect of the Laser Beam on the Skin: Preliminary Report," The Journal of Investigative Dermatology 40: 121-122 (1963).

Goldman et al., "Effect of the Laser Beam on the Skin: III. Exposure of Cytological Preparations," The Journal of Investigative Dermatology: 247-251 (1963).

Goldman et al., "Pathology of the Effect of the Laser Beam on the Skin," Nature 197(4870): 912-914 (1963).

Goldman et al., "The Biomedical Aspects of Lasers," JAMA 188(3): 230-234(1964).

Goldman et al., "Impact of the Laser on Nevi and Melanomas," Archives of Dermatology 90: 71-75(1964).

Goldman et al., "The Effect of Repeated Exposures to Laser Beams," Acta Dermato-Venerologica 44: 264-268 (1964).

Gossman et al., "Experimental Comparison of Laser and Cryosurgical Cilia Destruction," Ophthalmic Surgery 23(3): 179-182 (1992).

Gossman et al., "Prospective Evaluation of the Argon Laser in the Treatment of Tichiasis," Ophthalmic Surgery 23(3): 183-187 (1992).

Grekin et al., "Tin Ethyl Etiopupurin (SnET2): Phase I/II Clinical Results for the Treatment of Aids-Related Cutaneous Kaposi's Sarcomas at the University of California, San Francisco," Abstract 207, American Society for Laser Medicine and Surgery Abstracts 44.

Grossman et al., "Damage to Hair Follicles by Normal-Mode Ruby Laser Pulses," Journal of the American Academy of Dermatology 35: 889-894 (1996).

Grossman et al., "PDT for Hirsutism," Abstract 205, American Society for Laser Medicine and Surgery Abstracts 44.

Gustafsson et al., "A Variable Pulsewidth Vascular System for Dermatology," SPIE, 2128: 188-196 (1994).

Haina et al., "Possibilities for the Increase of the Coagulation Depth in Skin with the Argonlaser," in Waidelich W, ed: Springer, Berlin-Heidelberg-New York-Tokyo (1987).

Haina et al., "Improvement of Therapy Results in Treatment of Port Wine Stains with the Argonlaser," in Waidelich W, eds: Springer, Berlin-Heidelberg-New York-Tokyo (1987).

Hellwig et al., "Treatment of Vascular Malformations and Benign Pigmented Lesions by Pulsed Dye Laser, Photoderm VL, and Q-Switched Ruby Laser,"(Abstract) Laryngo-Rhino-Otol. 74: 634-641 (1995).

Huerter et al., "Multiple Eruptive Vellus Hair Cysts Treated with Carbon Dioxide Laser Vaporization," Journ. Dermatol. Surg. Oncol. 13(3): 260-263 (1987).

Iwasaki et al., "Development of Laser Systems for Treatment of Hyperpigmented Skin Lesions," Japanese Journal of Medical Electronics and Biological Engineering 27: 26-34 (1989).

Khan et al., "Optical Clearing of In Vivo Human Skin: Implications for Light-Based Diagnostic Imaging and Therapeutics," Lasers in Surgery and Medicine 34: 83-85 (2004).

Khan et al., "Can Topically Applied Optical Clearing Agents Increase the Epidermal Damage Threshold and Enhance Therapeutic Efficacy?" Lasers in Surgery and Medicine 35: 93-95 (2004).

Kincade, K., "First Laser Hair-Removal System Gains FDA Clearance," Laser Focus World Jun. 1995.

Raulin et al., "Effective Treatment of Hypertrichosis with Pulsed Light: A Report of Two Cases," Ann. Plast. Surg. 39: 169-174 (1997).

Riggle et al., "Laser Effects on Normal and Tumor Tissue," Laser Applications in Medicine and Biology 1: 35-65 (1971).

Rosenfeld et al., "Treatment of Cutaneous and Deep Vascular Lesions with the Nd: YAG Laser," Lasers in Surgery and Medicine 6: 20-23 (1986).

Rosenfeld et al., "The Treatment of Cutaneous Vascular Lesions with the ND: YAG Laser," Annals of Plastic Surgery 21 (3): 223-230 (1988).

Schirmer, K., "Simultaneous Thermal and Optical Breakdown Mode Dual Laser Action," Ophthalmologica 205: 169-177 (1992).

Shapshay et al., "Neodymium-YAG Laser Photocoagulation of Hemangiomas of the Head and Neck," Laryngoscope 97: 323-330 (1987).

Shimbashi et al., "Ruby Laser Treatment of Pigmented Skin Lesions," Aesthetic Plastic Surgery 19: 225-229 (1995).

Smartlipo: Laser Lipolysis With Pulsed Nd: YAG Laser Brochure, DEKA M.E.L.A. s.r.l., Italy, 2 pages.

Smoothbeam Brochure, Candela Corporation, 6 pages (2004).

Solomon et al., "Histopathology of the Laser Treatment of Port-Wine Lesions: Biopsy Studies of Treated Areas Observed up to Three Years After Laser Impacts," The Journal of Investigative Dermatology 50(2): 141-146 (1968).

Stewart, M., "Sebaceous Gland Lipids," Seminars in Dermatology, 11(2): 100-105 (1992).

Svaasand et al., "Melanosomal Heating During Laser Induce Photothermolysis of Port Wine Stains," Abstract 233, American Society for Laser Medicine and Surgery Abstracts (1995).

Svaasand et al., "Epidermal Heating During Laser Induced Photothermolysis of Port Wine Stains: Modeling Melanosomal Heating After Dynamic Cooling the Skin Surface," SPIE 2323: 366-377 (1994).

Takata et al., "Laser-Induced Thermal Damage of Skin," SAM-TR-77-38, USAF School of Aerospace Medicine (1977).

Tanino et al., "Development of Ruby Laser System for Medical Use," (Abstract) Journal of the Japanese Society for Laser Surgery and Medicine 11(4): 93-98 (1991).

Taylor et al., "Treatment of Tattoos by Q-Switched Ruby Laser," Arch. Dermatol. 126: 893-899 (1990).

"Tech News: Lasers and Hair," Circle 21: (1983).

Tranner et al., "Photodynamic Synovectomy with Benzoporphyrin Derviative in a Rabbit Model of Rheumatoid Arthritis," Abstract 204, American Society for Laser Medicine and Surgery Abstracts 44.

Tri-Active Brochure, DEKA M.E.L.A. s.r.l., Italy, 4 pages.

Tsai et al., "Near-infrared Absorption Property of Biological Soft Tissue Constituents," Journal of Medical and Biological Engineering 21(1): 7-14 (2001).

van Gemert et al., "Is There an Optimal Laser Treatment for Port Wine Stains?," Lasers Surg. Med., 6: 76-83 (1986).

van Gemert et al., "Limitations of Carbon Dioxide Lasers for Treatment of Port Wine Stains," Arch. Derm., 123: 71-73 (1987).

van Gemert et al., "Temperature Behavior of a Model Port-Wine Stain During Argon Laser Coagulation," Phys. Med. Biol. 27(9): 1089-1104 (1982).

Waldman et al., "Cutaneous Inflammation: Effects of Hydroxy Acids and Eicosanoid Inhibitors on Vascular Permeability," Abstracts 523, 88(4): (1987).

Wang et al., "Characterization of Human Scalp Hairs by Optical Low-Coherence Reflectometry," Optics Letters 20(6): 524-526 (1995).

Warren et al., "Pigmentation Induction by Melanocyte Stimulating Hormone in Human Skin Culture," Abstracts 523, 88(4): (1987).

Wastek et al., "Characterization of H-Substance P (SP) Binding to a Mouse Monoclonal Mast Cell Line (MC/9)," Abstracts 523, 88(4): (1987).

Watanabe et al., "The Effect of Pulse Duration on Selective Pigmented Cell Injury by Dye Lasers," Abstracts 523, 88(4): (1987).

Watanabe et al., "Comparative Studies of Femtosecond to Microsecond Laser Pulses on Selective Pigmented Cell Injury in Skin," Photochemistry and Photobiology 53(6): 757-761 (1991).

Weissman et al., "Growth, Collagen and Glycosaminoglcan Synthesis by Dermal Fibroblasts Derived From Puva Treated and Psoriatic Patients," Abstracts 523, 88(4): (1987).

International Search Report for International Application No. PCT/US2006/001112, Date of Mailing Sep. 20, 2006 (7 pages).

Communication Relating to the Results of the Partial International Search, International Application No. PCT/US2006/001112, Mailed May 26, 2006, pp. 1-2.

Alster, T., "Laser Hair Removal: Are the Results Permanent?," Laser Focus: 21-23 (1993).

Anderson et al., "The Optics of Human Skin," The Journal of Investigative Dermatology 77(1): 13-19 (1981).

Anderson et al., "Lasers in Dermatology Provide a Model for Exploring New Applications in Surgical Oncology," International Advances in Surgical Oncology 5: 341-358 (1982).

Anderson et al., "Selective Photothermolysis: Precise Microsurgery by Selective Absorption of Pulsed Radiation," Science 220: 524-527 (1983).

Anderson, R., "Optics of the Skin," in Clinical Photomedicine, ed: Marcel Dekker Inc., New York, New York, 28-31 (1993).

Anderson et al., "Fractional Photothermolysis Redefines Facial Skin Regeneration Science," Aesthetic Buyers Guide Mar./Apr. 2004.

Anvari et al., "Selective Cooling of Biological Tissues During Pulsed Laser Irradiation," Abstract 17, American Society for Laser Medicine and Surgery Abstracts (1995).

Anvari et al., "Dynamic Epidermal Cooling in Conjunction with Laser Treatment of Port-Wine Stains: Theoretical and Preliminary Clinical Evaluations," Lasers in Medical Science 10: 105-112 (1995).

Anvari et al., "A Theoretical Study of the Thermal Response of Skin to Cryogen Spray Cooling and Pulsed Laser Irradiation: Implications for Treatment of Port Wine Stain Birthmarks," Phys. Med. Biol. 40: 1451-1465 (1995).

Anvari et al., "Selective Cooling of Biological Tissues: Application for Thermally Mediated Therapeutic Procedures," Phys. Med. Biol. 40: 241-252 (1995).

Awan, K., "Argon Laser Treatment of Trichiasis," Ophthalmic Surgery 17(10): 658-660 (1986).

Goldman et al., "Radiation From a Q-Switched Ruby Laser," The Journal of Investigative Dermatology: 69-71 (1964).

Goldman et al., "Treatment of Basal Cell Epithelioma by Laser Radiation," JAMA 189(10): 773-775 (1964).

Goldman, L., "Comparison of the Biomedical Effects of the Exposure to Low and High Energy Lasers," Annals of New York Academy of Sciences, 802-831 (1965).

Goldman, L., "Dermatologic Manifestations of Laser Radiation," Proceedings of the First Annual Conference on Biologic Effects of Laser Radiation, Federation of American Societies for Experimental Biology, Supp. No. 14: S-92-S-93 (Jan.-Feb. 1965).

Goldman et al., "Laser Action at the Cellular Level," JAMA 198(6): 641-644 (1966).

Goldman et al., "Investigative Studies With Quartz Rods for High Energy Laser Transmission," Medical Research Engineering: 12-17 (1967).

Goldman et al., "Laser Treatment of Tattoos," JAMA 201(11): 841-844 (1967).

Goldman et al., "Replica Microscopy and Scanning Electron Microscopy of Laser Impacts on the Skin," The Journal of Investigative Dermatology 32(1): 18-24 (1968).

Goldman et al., "Investigative Studies with the Laser in the Treatment from Basal Cell Epitheliomas," Southern Medical Journal 61: 735-742 (1968).

Goldman, L., "The Skin," Arch. Environ. Health 18: 434-436 (1969).

Goldman et al., "Preliminary Investigation of Fat Embolization for Pulsed Ruby Laser Impacts of Bone," Nature 221: 361-363 (1969).

Goldman et al., "Long-Term Laser Exposure of a Senile Freckle," Arch. Environ Health 22: 401-403 (1971).

Goldman et al., "The Laser in Dermatology," Lasers in Medicine, ed: Gordon and Breach, New York, New York: 329-352 (1971).

Goldman, L., "Effects of New Laser Systems on the Skin," Arch. Dermatol. 108: 385-390 (1973).

Goldman, L., "Laser Surgery for Skin Cancer," New York State Journal of Medicine: 1897-1900 (1977).

Goldman, L., "Surgery by Laser for Malignant Melanoma," J. Dermatol. Surg. Oncol. 5(2): 141-144 (1979).

Kincade, K., "New Procedures Push Tissue Studies Beneath the Surface," Laser Focus World August: 57-63 (1995).

Klein et al., "Biological Effects of Laser Radiation I: Threshold Studies and Reversible Depigmentation in Rodent Skin," Nerem Record: 108-109 (1965).

Kuhns et al., "Biological Effects of Laser Radiation II: Effects of Laser Irradiation on the Skin," Nerem Record: (1965).

Kuhns et al., "Laser Injury in Skin," Laboratory Investigation 17(1): 1-13 (1967).

Kuriloff, et al., "Pharyngoesophageal Hair Growth: The Role of Laser Epilation," Case Reports 98(4): 342-345 (1988).

Landthaler et al., "Neodymium-YAG Laser Therapy for Vascular Lesions," Journal of the American Academy of Dermatology 14(1): 107-117 (1986).

Landthaler et al. "Laser Treatment of Port Wine Stains," Dermatologica: Letters to the Editor 175: 156-160 (1987).

Laor et al., "The Pathology of Laser Irradiation of the Skin and Body Wall of the Mouse," Laser Irradiation 47(4): 643-663 (1965).

Lask et al., "Neodymium: Yttrium-Aluminum-Garnet Laser for the Treatment of Cutaneous Lesions," Clinics in Dermatology 13: 81-86 (1995).

Lask et al., "Nonablative Laser Treatment of Facial Rhytides," SPIE 2970: 338-349 (1997).

Lui et al., "Photodynamic Therapy of Malignant Skin Tumors with BPD Verteporfin (Benzoporphyrin Derivative)," Abstract 206, American Society for Laser Medicine and Surgery Abstracts 44.

Maiman, T., "Biomedical Lasers Evolve Toward Clinical Applications," Hospital Management: 39-41 (1966).

Manstein et al., "Fractional Photothermolysis: A New Concept for Cutaneous Remodeling Using Microscopic Patterns of Thermal Injury," Lasers in Surgery and Medicine, 34: 426-438 (2004).

Margolls et al., "Visible Action Spectrum for Melanin-Specific Selective Photothermolysis," Lasers in Surgery and Medicine 9: 389-397 (1989).

Matsumoto, et al., "Ruby Laser Treatment of Melanin Pigmented Skin Lesions Using Toshiba Model LRT-301A Ruby Laser," Journal of Japanese Society for Laser Surgery and Medicine 10(3): 451-454 (1989).

Meloy, T., "The Laser's Bright Magic," National Geographic: 858-881(1966).

Mester et al., "Effect of Laser Beam on the Hair Growth of Mice," Experimental Medicine 19: 628-631 (1967).

Mester et al., "The Stimulating Effect of Low Power Laser-Rays on Biological Systems," Laser Review: 3-6 (1968).

Mester et al., "Effect of Laser Rays on Would Healing," The American Journal of Surgery 122: 532-535 (1971).

Mester et al., "The Biomedical Effects of Laser Application," Lasers in Surgery and Medicine 5: 31-39 (1985).

Milner et al., "Dynamic Cooling for Spatial Confinement of Laser Induced Thermal Damage in Collagen," Abstract 262, American Society for Laser Medicine and Surgery Abstracts (1995).

Miyasaka et al., "Basic and Clinical Studies of Laser for Hyperpigmented Skin Lesions," Journal of the Japanese Society for Laser Surgery and Medicine 11: 117-127 (1991).

Nakaoka et al., "The Square and Uniform Intensity Ruby Laser for the Treatment of Pigmented Skin Lesions," European Journal of Plastic Surgery 15: 23-30 (1992).

Nelson et al., "Dynamic Cooling of the Epidermis During Laser Port Wine Stain Therapy," Abstract 253, American Society for Laser Medicine and Surgery Abstracts (1994).

Nelson et al., "Epidermal Cooling During Pulsed Laser Treatment of Selected Dermatoses," SPIE 2623: 32-39 (1995).

Nelson et al., "Dynamic Epidermal Cooling During Pulsed Laser Treatment of Port-Wine Stain," Arch Dermatol, 131: 695-700 (1995).

Nelson et al., "Dynamic Epidermal Cooling in Conjunction with Laser-Induced Photothermolysis of Port Wine Stain Blood Vessels," Lasers in Surgery and Medicine 19: 224-229 (1996).

Ohshiro et al., "The Ruby and Argon Lasers in the Treatment of Naevi," Annals Academy of Medicine 12(2): (1983).

Ohtsuka et al., "Histological Studies and Clinical Experiences of Ruby Laser Treatment," 107-115 (1991).

Oshry et al., "Argon Green Laser Photoepilation in the Treatment of Trachomatous Trichiasis," Ophthalmic Plastic and Reconstructive Surgery 10(4): 253-255 (1994).

Parrish et al., "Selective Thermal Effects with Pulsed Irradiation from Lasers: From Organ to Organelle," The Journal of Investigative Dermatology 80(6): 75s-80s (1983).

Polla et al., "Melanosomes Are a Primary Target of Q-Switched Ruby Laser Irradiation in Guinea Pig Skin," The Journal of Investigative Dermatology 89(3): 281-286 (1987).

Welch et al., "Evaluation of Cooling Techniques for the Protection of the Epidermis During Nd: YAG Laser Irradiation of Skin," in Neodymium-YAG Laser in Medicine and Surgery, ed: SN Joffe, Elsevier, New York: 196-204 (1983).

Werse et al., "Effects of Essential Fatty Acid Deficiency on the Structure and Function of Epidermal Lipids," Abstracts 523, 88(4): (1987).

"Workshop on Analysis of Laser-Tissue Interaction for Clinical Treatment," University of Texas, Austin, TX 78712, Jul. 14-18, 1986.

Yules et al., "The Effect of Q-Switched Ruby Laser Radiation on Dermal Tattoo Pigment in Man," Arch. Surg. 95: 179-180 (1967).

Zeitler et al., "Laser Characteristics that Might be Useful in Biology," Laser Applications in Medicine and Biology 1: 1-18 (1971).

* cited by examiner

METHOD AND APPARATUS FOR TREATING A DISEASED NAIL

CROSS-REFERENCE TO RELATED APPLICATIONS

This application claims the benefits of and priority to U.S. Provisional Patent Application Ser. No. 60/644,245 filed on Jan. 13, 2005, and U.S. Provisional Patent Application Ser. No. 60/656,356 filed on Feb. 25, 2005, both of which are owned by the assignee of the instant application and the disclosures of which are incorporated herein by reference in their entireties.

FIELD OF THE INVENTION

The invention generally relates to treating diseased nails, and more particularly to treating diseased nails using radiation and/or another form of energy to substantially deactivate the source of the disease.

BACKGROUND OF THE INVENTION

Thick, discolored, disfigured, and/or split nails can be common symptoms of disease of a fingernail or toenail. This disease can be caused by bacteria, mold, a fungus, viruses, parasites, or other organisms or microorganisms, and if left untreated, the disease can result in partial or complete destruction of a patient's nail plate.

In general, the most common type of nail disease is onychomycosis, which can be caused by a fungus, such as, a dermatophyte that can invade the nail plate and nail bed forming a patient's nail. Creams, ointments, oral medications, and radiation can be used to treat onychomycosis or other nail diseases. These treatments, however, may not eliminate the source of the disease, do not work for many patients, and can cause numerous side effects in patients.

SUMMARY OF THE INVENTION

The invention, in various embodiments, features a method and apparatus to treat a diseased nail using radiation and/or another form of energy. A treatment can eliminate or substantially eliminate the source of disease in the nail. An organism causing the disease can be deactivated. In one embodiment, the organism is thermally deactivated by delivering energy or radiation to a target area, which can be adjacent the organism or can include the organism. Tissue surrounding the organism itself can absorb radiation and transfer thermal energy to the organism to deactivate the organism, and/or the organism can absorb directly the radiation. Deactivation of the organism can render it unable to grow, reproduce and/or replicate, and, in some embodiments, can destroy the organism. Deactivation can result from thermal destruction of the organism, from denaturing or partially denaturing one or more molecules forming the organism, from initiating a photobiological or photochemical reaction that attacks the organism, and/or from inducing an immune response that attacks the organism.

A nail treatment can be performed by a medical professional without the use of a dying agent or an exogenous chromophore, and can be effective at eliminating the source of the disease without subjecting a patient to adverse side effects. Examples of organisms causing disease in a nail that can be treated include, but are not limited to, bacteria, mold, fungi, viruses, parasites, other microorganisms, and any combination thereof. The organism can be a dermatophyte, such as, for example, epidermophyoton floccosum, trichophyton rubrum, or trichophyton mentagrophyte.

In one aspect, the invention features a method of treating a diseased nail having a nail bed and a nail plate. The method includes delivering a beam of radiation to a target area to thermally deactivate an unwanted organism without causing substantial unwanted injury to the nail bed and/or the nail plate. The beam of radiation can have a wavelength in excess of about 400 mm.

In another aspect, the invention features a method of treating a diseased nail having a nail bed and a nail plate. The method includes delivering a pulsed beam of radiation to a target area. The radiation absorbed is converted to thermal energy that is trapped by the nail plate of the diseased nail. An unwanted organism in at least one of the nail bed and the nail plate can be thermally deactivated without causing substantial unwanted injury to the nail bed and/or the nail plate of the diseased nail. The temperature in the region where the unwanted organism resides can be raise sufficiently to deactivate the organism, but not high enough to result in unwanted injury to the surrounding tissue.

In yet another aspect, the invention features an apparatus for treating a diseased nail having a nail plate and a nail bed. The apparatus includes an energy source, and a system for delivering a beam of radiation provided by the energy source to a target area. An unwanted organism in the nail bed and/or the nail plate is thermally deactivated without causing substantial unwanted injury to the nail bed and/or the nail plate of the diseased nail. The apparatus also includes a device to position an appendage having the diseased nail during treatment.

In still another aspect, the invention features an apparatus for treating a diseased nail having a nail bed and a nail plate. The apparatus includes means for delivering a beam of radiation to a target area to thermally deactivate an unwanted organism without causing substantial unwanted injury to the nail bed and/or the nail plate. The beam of radiation can have a wavelength in excess of about 400 nm.

In another aspect, the invention features a method of treating a diseased nail having a nail bed and a nail plate. The method includes delivering a beam of radiation to a target area of the diseased nail to cause the temperature of the target area to be raised to a level sufficient to substantially deactivate an unwanted organism in the diseased nail without causing substantial unwanted injury to surrounding tissue.

In yet another aspect, the invention features an apparatus for treating a diseased nail having a nail bed and a nail plate. The apparatus includes means for delivering a pulsed beam of radiation to a target area. The radiation absorbed is converted to thermal energy that is trapped by the nail plate of the diseased nail. An unwanted organism in at least one of the nail bed and the nail plate can be thermally deactivated without causing substantial unwanted injury to the nail bed and/or the nail plate of the diseased nail.

In another aspect, the invention features an apparatus for treating a diseased nail having a nail bed and nail plate. The apparatus includes means for delivering a continuous beam of radiation to a target area. The beam of radiation can be turned off when sufficient heating of the target area has been achieved.

In other examples, any of the aspects above, or any apparatus or method described herein, can include one or more of the following features. In one embodiment, the method includes irradiating the target area such that radiation absorbed is converted to thermal energy. The nail plate of the diseased nail can trap the thermal energy to thermally deactivate the unwanted organism present in the nail bed and/or the nail plate. In various embodiments, the beam can be delivered until occurrence of an event (e.g., a patient event such as a patient having the diseased nail indicating a sensation of pain or a predetermined event such as delivering a predetermined number of pulses).

In some embodiments, the method can include delivering a pulsed beam of radiation to the diseased nail. The pulsed beam can be moved after each pulse. Substantially all of the nail bed can be irradiated by moving the beam of radiation. In one embodiment, after an interval of time, a second series of pulses of radiation can be delivered, and the second series of pulses can irradiate substantially all of the nail bed. In various embodiments, the beam of radiation can be delivered at a rate of one pulse per second.

In one embodiment, the method includes inducing an immune response to at least partially deactivate the organism. In one embodiment, at least a portion of the beam of radiation is absorbed by the organism. In one embodiment, the target area includes at least one blood vessel in the nail bed. In one embodiment, the junction of the nail bed and the nail plate is selectively irradiated to treat the diseased nail. Thermal deactivation can include killing the organism.

In one embodiment, the radiation is absorbed by a target chromophore in the target area in the absence of an exogenously applied chromophore or photosensitizer. The organism can be one or more of a bacterium, a mold, a fungus, a virus, and a parasite. In one embodiment, the fungus is a dermatophyte (e.g., epidermophyton floccosum, trichophyton rubrum, and trichophyton mentagrophyte).

In various embodiments, a laser, a radio-frequency generator or a microwave generator can be used to provide the beam of radiation. The laser can be a pulsed dye laser. In some embodiments, the beam of radiation can have a wavelength between about 400 nm and about 1,100 nm (e.g., between about 585 nm and about 600 nm). In some embodiments, the beam of radiation can have a fluence in the range of about 4 $J/cm^2$ to about 20 $J/cm^2$. The beam of radiation can have a spotsize of between about 2 mm and about 20 mm. In some embodiments, the beam of radiation has a pulsewidth equal to or less than the thermal relaxation time of the organism.

In various embodiments, the method includes introducing an index matching solution into a porous region of the diseased nail prior to delivering the radiation. The index matching solution can be one or more of mineral oil, glycerin, glycol, and water.

The radiation from the energy source can be scanned over an exposed surface of the disease nail during a treatment. In some embodiments, the radiation can be scanned over the exposed surface multiple times (e.g., two times, three times, four times) per treatment. The treatment can be performed by a medical professional a single time on a diseased nail, or, in some embodiments, at least twice (e.g., two or more visits to the medical professional for treatment). One or more treatments can be followed by the application of a topical cream or an ointment to the diseased nail, the cuticle, and/or surrounding tissue or by administering a medication (e.g., oral or intravenous) to prevent reoccurrence of the unwanted organism or to eliminate the unwanted organism.

Other aspects and advantages of the invention will become apparent from the following drawings, detailed description, and claims, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE INVENTION

Figure 1:
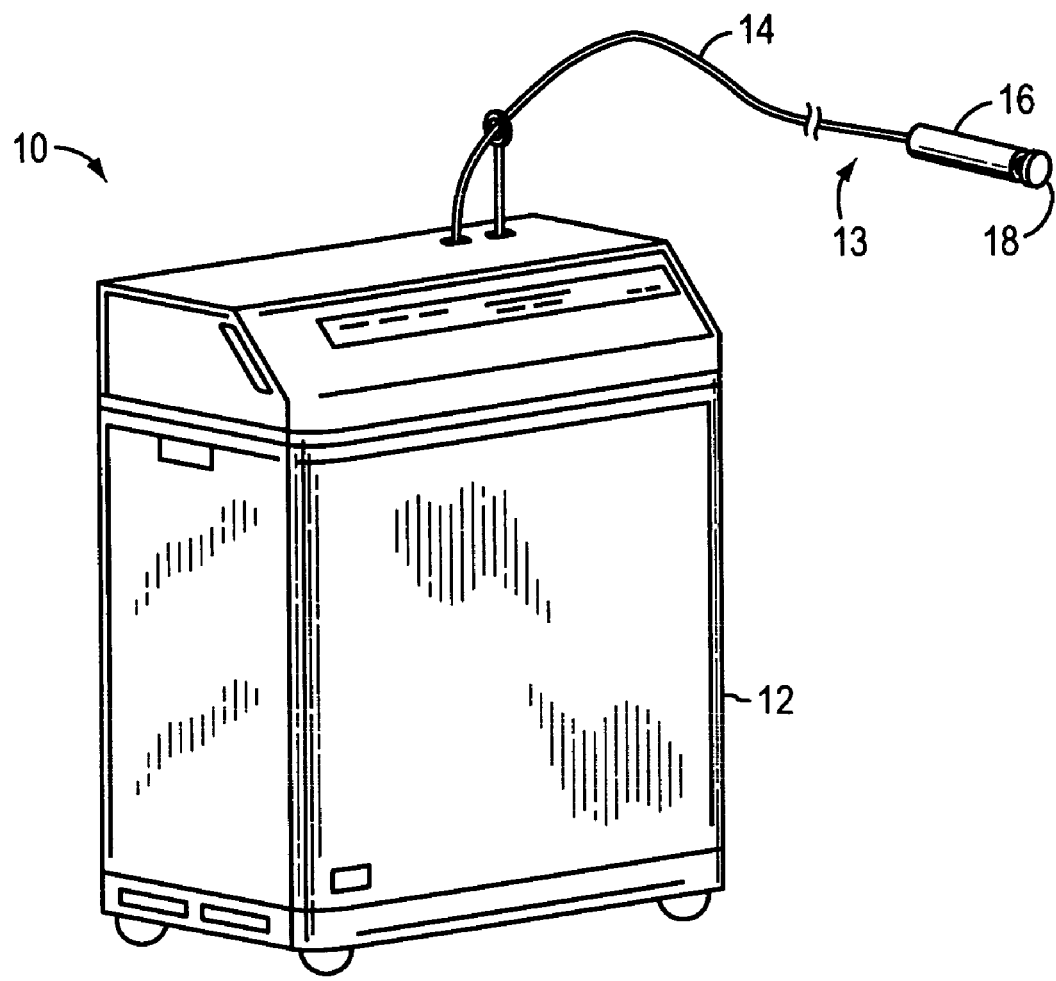
FIG. 1 depicts a perspective view of an exemplary apparatus for treating a diseased nail according to the invention.

FIG. 1 shows an exemplary embodiment of a system 10 for treating a nail having a disease. The system 10 includes an energy source 12 and a delivery system 13. In one embodiment, a beam of radiation provided by the energy source 12 is directed via the delivery system 13 to a target region of a diseased nail having at least a nail bed and a nail plate. The target region can be a target area or a target volume of tissue. In the illustrated embodiment, the delivery system 13 includes a fiber 14 having a circular cross-section and a handpiece 16. A beam of radiation can be delivered by the fiber 14 to the handpiece 16, which can include an optical system (e.g., an optic or system of optics) to direct the beam of radiation to the target region of the diseased nail. A user can hold or manipulate the handpiece 16 to irradiate the target region. The delivery system 13 can be positioned in contact with the diseased nail, can be positioned adjacent the diseased nail, or can be positioned proximate the diseased nail. In the embodiment shown, the delivery system 13 includes a spacer 18 to space the delivery system 13 from the skin surface. In one embodiment, the spacer 18 can be a distance gauge.

In various embodiments, the energy source 12 can be an incoherent light source, a coherent light source (e.g., a laser), a microwave generator, or a radio-frequency generator. In one embodiment, the source generates ultrasonic energy that is used to treat the diseased nail. In some embodiments, two or more sources can be used together to effect a treatment. For example, an incoherent source can be used to provide a first beam of radiation while a coherent source provides a second beam of radiation. The first and second beams of radiation can share a common wavelength or can have different wavelengths. In an embodiment using an incoherent light source or a coherent light source, the beam of radiation can be a pulsed beam, a scanned beam, or a gated CW beam. The delivery system 13 can include a cooling apparatus for cooling a nail before, during, or after treatment.

In various embodiments, the beam of radiation can have a wavelength between about 250 nm and about 2,600 nm, although longer and shorter wavelengths can be used depending on the application. In some embodiments, the wavelength can be between about 400 nm and about 1,800 nm. In some embodiments, the wavelength can be between about 400 nm and about 1,100 nm. In some embodiments, the wavelength can be between about 1,160 nm and about 1,800 nm. In some embodiments, the wavelength can be between about 400 nm and about 700 nm. In one embodiment, the wavelength is between about 500 nm and about 600 nm. In one detailed embodiment, the wavelength is about 585 nm or about 600 nm. One or more of the wavelengths used can be within a range of wavelengths that are transmitted by the nail plate of the diseased nail.

Exemplary lasers include, but are not limited to, pulsed dye lasers, Nd:YAG lasers, frequency doubled Nd:YAG lasers, Nd:glass lasers, copper vapor lasers, alexandrite lasers, frequency doubled alexandrite lasers, titanium sapphire lasers, ruby lasers, fiber lasers, and diode lasers. Exemplary pulsed dye lasers include V-Beam brand lasers and C-Beam brand lasers, both of which are available from Candela Corporation (Wayland, Mass.). Exemplary incoherent light sources include, but are not limited to, intense pulsed light sources, arc lamps, and flashlamps (e.g., an argon or xenon lamp). An incoherent light source can include one or more filters to cutoff undesired wavelengths. For example, an ultra-violet filter (e.g., a filter that cuts off wavelengths less than about 350 nm) and/or a red or infra-red filter (e.g., a filter that cuts off wavelengths greater than about 700 nm) can be used together with an incoherent light source to provide a beam of radiation to treat a nail. An exemplary incoherent light source is an Ellipse system available from Danish Dermatologic Development A/S (Denmark).

In various embodiments, the beam of radiation can have a fluence between about 1 $J/cm^2$ and about 50 $J/cm^2$, although higher and lower fluences can be used depending on the application. In some embodiments, the fluence can be between about 2 $J/cm^2$ and about 20 $J/cm^2$. In one embodiment, the fluence is between about 4 $J/cm^2$ and about 10 $J/cm^2$.

In various embodiments, the beam of radiation can have a spotsize between about 1 mm and about 25 mm, although larger and smaller spotsizes can be used depending on the application. In some embodiments, the spotsize can be between about 2 mm and about 20 mm. In one detailed embodiment, the spotsize is 7 mm.

In various embodiments, the beam of radiation can have a pulsewidth between about 10 μs and about 30 s, although larger and smaller pulsewidths can be used depending on the application. In some embodiments, the pulsewidth can be between about 100 μs and about 1 s. In one detailed embodiment, the pulsewidth can be about 100 μs, about 500 μs, about 1 ms, about 5 ms, about 10 ms, about 50 ms, about 100 ms, about 500 ms, or about 1 s.

In various embodiments, the beam of radiation can be delivered at a rate of between about 0.1 pulse per second and about 10 pulses per second, although faster and slower pulse rates can be used depending on the application. In one detailed embodiment, the pulse rate is about 1 pulse per second.

Figure 2:
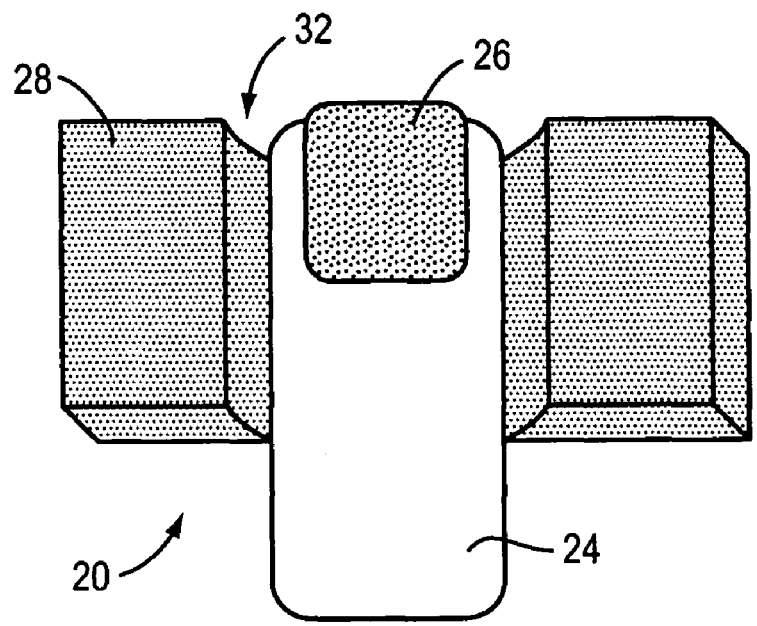
FIG. 2 shows a perspective view of an exemplary apparatus for holding an appendage having a diseased nail during treatment according to the invention.
Figure 3:
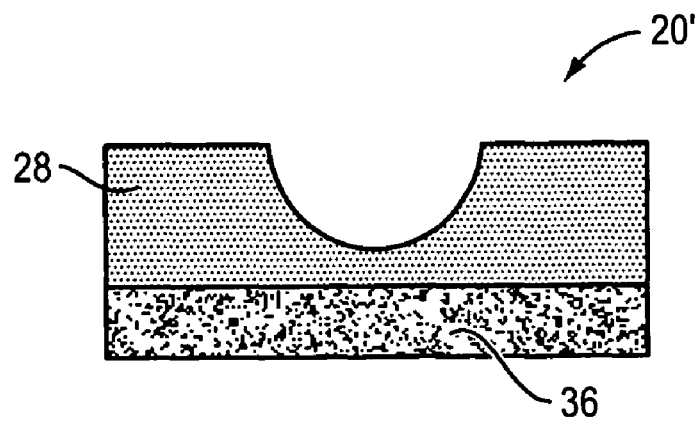
FIG. 3 shows a sectional view of another exemplary apparatus for holding an appendage having a diseased nail during treatment according to the invention.

FIG. 2 shows an exemplary apparatus 20 for positioning a patient's appendage 24 (e.g., a finger or a toe) having a diseased nail 26. The apparatus 20 includes a base 28 defining an opening 32 for retaining or cradling the appendage 24 during a treatment. FIG. 3 shows an exemplary embodiment of an apparatus 20' including a cooling pad 36. Cooling can facilitate a treatment and can reduce a patient's sensitivity to pain. The cooling pad 36 can be placed below the appendage 24, or can be affixed to the base 28 to cool the appendage 24. The cooling pad 36 can be filled with ice, a frozen gel pack, or a cooling fluid. In one embodiment, a system for treating a diseased nail 26 includes an energy source 12, a delivery system 13 for applying energy to the appendage 24 having the diseased nail 26, and an apparatus 20 for positioning the appendage during treatment.

To minimize thermal injury to tissue surrounding the diseased nail 26, the delivery system 13 shown in FIG. 1 can include a cooling system for cooling the nail plate before, during or after delivery of radiation. Cooling can include contact conduction cooling, evaporative spray cooling, convective air flow cooling, or a combination of the aforementioned. In one embodiment, the handpiece 16 includes a nail contacting portion that can be brought into contact with the region of the diseased nail receiving the beam of radiation. The nail contacting portion can cool the nail plate. The nail contacting portion can include a sapphire or glass window and a fluid passage containing a cooling fluid. The cooling fluid can be a fluorocarbon type cooling fluid, which can be transparent to the radiation used. The cooling fluid can circulate through the fluid passage and past the window contacting the nail plate.

A spray cooling device can use cryogen, water, or air as a coolant. In one embodiment, a dynamic cooling device can be used to cool the nail plate and/or surrounding tissue (e.g., a DCD available from Candela Corporation). For example, the delivery system 13 shown in FIG. 1 can include tubing for delivering a cooling fluid to the handpiece 16. The tubing can be connected to a container of a cold fluid, and the handpiece can include a valve for delivering a spurt of cold fluid to the nail plate. Heat can be extracted from the nail plate by virtue of evaporative cooling of the cold fluid. The fluid can be a non-toxic substance with high vapor pressure at normal body temperature, such as a Freon or tetrafluoroethane.

Figure 4:
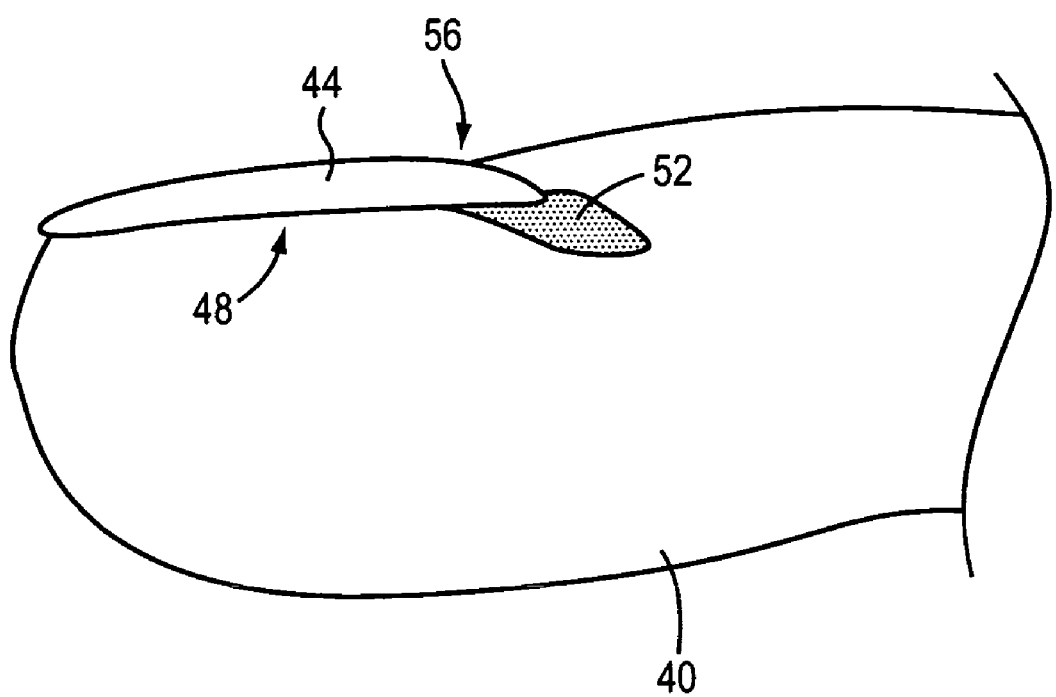
FIG. 4 shows a sectional view of an exemplary appendage (e.g., a finger or a toe).

FIG. 4 shows a sectional view of an appendage 40 (e.g., a finger or a toe) including a nail plate 44, a nail bed 48, and nail root 52. The nail plate 44 can be formed from a number of horny plates extending from the nail root 52 and cuticle 56. The nail 44 is positioned over and protects the nail bed 48. One or more organisms can invade or permeate the nail plate 44, the nail bed 48, the nail root 52, or the nail matrix to cause an infection or disease in the nail.

Figure 5:
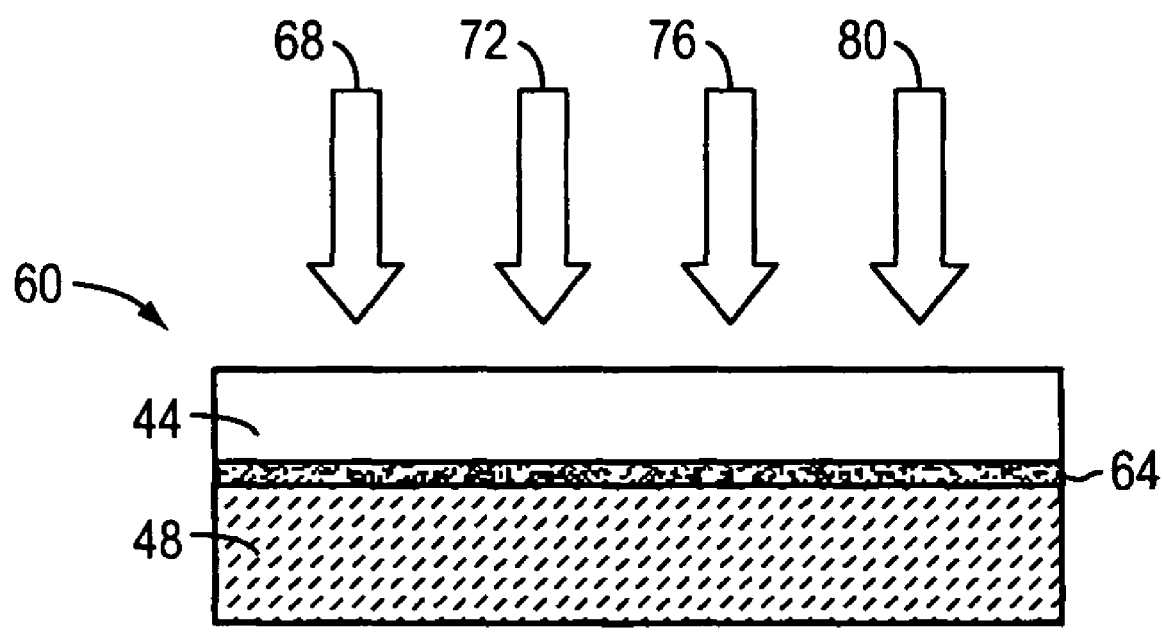
FIG. 5 depicts a sectional view of an exemplary nail being irradiated according to the invention.

FIG. 5 depicts irradiation of a section of an exemplary nail 60 having the nail plate 44, the nail bed 48, and an unwanted organism causing disease 64 in the nail 60. A beam of radiation 68 is applied to a target area of the nail 60. The target area can be a portion of the nail plate 44, a portion of the nail bed 48, a portion of the disease 64, the unwanted organism itself, or any combination thereof. Chromophores in the nail plate 44 and nail bed 48 can include, but are not limited to, a blood vessel, a wall of a blood vessel, melanin, water, collagen, a blood cell, hemoglobin, plasma, the disease causing organism, or any combination thereof. Energy from the beam of radiation 68 can be absorbed by the target area and converted to thermal energy to deactivate the unwanted organism. The beam of radiation 68 can deactivate the unwanted organism without causing unwanted injury or substantial permanent injury to the nail plate 44 and/or the nail bed 48. In various embodiments, energy can be delivered at a predetermined wavelength, a predetermined pulsewidth, and a predetermined energy or fluence.

The unwanted organism can live and breed in and/or around the area of the junction between the nail plate 44 and the nail bed 48. The organism can get its nutrition from the nail plate 44 and can get moisture from the nail bed 48 to sustain itself. In some embodiments, to effectively treat the nail disease, energy can be directed selectively to a target area proximate to a bottom portion of the nail plate 44 and a top portion of the nail bed 48 to deactivate the unwanted organism. In one embodiment, the unwanted organism is thermally deactivated as the target area absorbs the beam of radiation and transfer the thermal energy to the unwanted organism.

In various embodiments, the beam of radiation can be selected to pass through the nail plate 44 and to be absorbed by the nail bed 48 (e.g., a top portion of the nail bed) and/or the unwanted organism. For example, the beam of radiation can be transmitted or substantially transmitted through the nail plate 44 to avoid heating the nail plate 44 as a whole. When the nail plate is heated as a whole, it can remain hot for an extended period of time, which can lead to unwanted injury to the surrounding tissue. Tissue injury depends not only on temperature, but also on the length of time at an elevated temperature. By selectively depositing energy to the nail plate 44, the nail bed 48, and/or the junction region therebetween, one can maximize the injury to the disease causing organism while minimizing injury to the surrounding tissue. In various embodiments, the tissue can be heated to a temperature of between about 50° C. and about 80° C., although higher and lower temperatures can be used depending on the application. In one embodiment, the temperature is between about 55° C. and about 70° C.

In some embodiments, a pulsed light source is used to selectively deliver the beam of radiation to a target area including the nail bed 48 and/or the unwanted organism. This can result in the temperature in the junction region between the nail plate 44 and the nail bed 48 being increased to thermally deactivate the unwanted organism without causing substantial unwanted injury or substantial permanent injury to surrounding tissue. In various embodiments, the radiation can also deactivate the unwanted organism by denaturing or partially denaturing one or more molecules forming the unwanted organism, by initiating a photobiological or photochemical reaction that attacks the organism, and/or by inducing an immune response that attacks the organism. In some embodiments, one or more of these mechanisms is induced by the beam of radiation to treat the diseased nail.

In various embodiments, the pulsed beam of radiation is scanned over the surface of the disease nail during a treatment. That is, the beam of radiation can be moved after delivery of one or more pulses. In one embodiment, the beam of radiation is moved after a single pulse. The pulse rate can be one pulse per second, although other suitable pulse rates can be used. The beam of radiation can be moved until the entire surface of the diseased nail has been substantially completely irradiated.

Referring to FIG. 5, the beam of radiation 68 is applied to a first position. The beam of radiation can be moved to at least a second position 72, a third position 76, and a fourth position 80. The beam can be moved in a linear fashion, in a predetermined pattern, or in a random fashion across the surface of the diseased nail. In some embodiments, the radiation can be scanned over the surface of the diseased nail multiple times during a treatment. The radiation can be scanned until the occurrence of an event, such as, for example, a patient indicating a sensation of pain, reaching a predetermined number of cycles of treatment, or reaching a predetermined number of pulses of radiation. In addition, treatment can be performed a single time, or multiple times over a course of hours, days, weeks, or months.

One or more treatments can be followed by the application of a topical cream or an ointment to the diseased nail, the cuticle, and/or surrounding tissue or by administering a medication (e.g., oral or intravenous) to prevent reoccurrence of the unwanted organism or to eliminate the unwanted organism. In one embodiment, a diseased nail can be scraped to remove excess growth prior to applying energy to the diseased nail.

Figure 6:
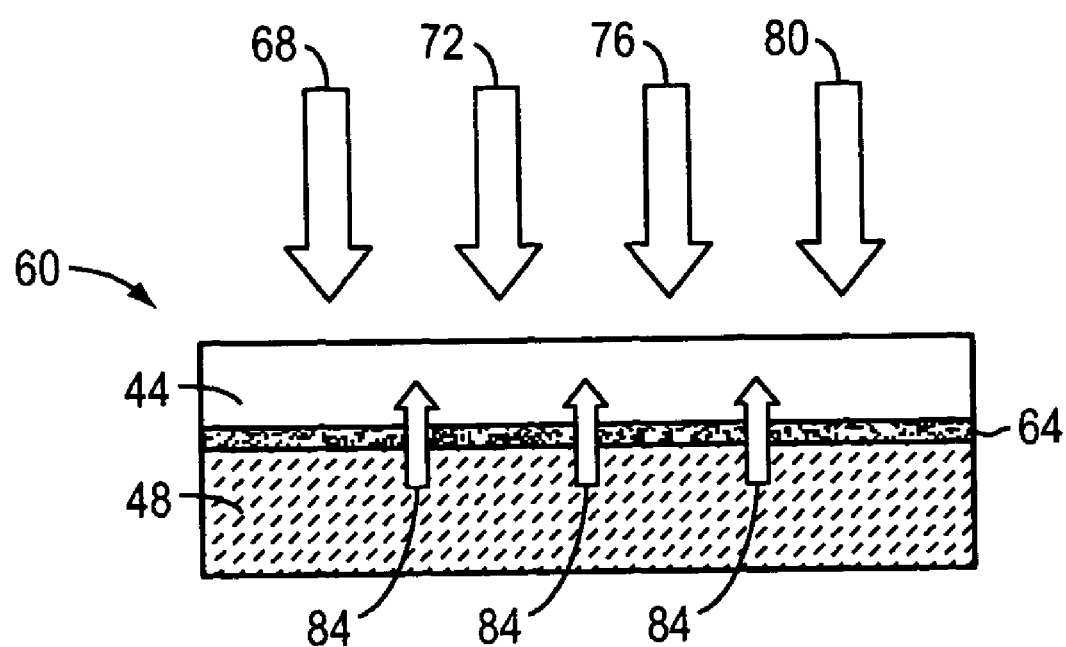
FIG. 6 shows a sectional view of another exemplary nail being irradiated according to the invention.

FIG. 6 shows another exemplary embodiment of irradiation of a section of the exemplary nail 60. According to the illustrated embodiment, the beams of radiation 68, 72, 76, and 80 applied to the target area are absorbed by the nail bed 48 and/or the unwanted organism. The energy is converted to thermal energy 84 that is trapped by the nail plate 44. The unwanted organism is not destroyed directly by the radiation; instead, thermal energy 84 trapped by the nail plate 44 deactivates the unwanted organism to treat the diseased nail 60. As the beam of radiation is scanned across the surface of the diseased nail, e.g., over a period of seconds, the temperature of the nail bed 48 can increase until the temperature is high enough that the patient starts to feel pain or until a predetermined number of pulses is delivered. The temperature of the junction region near the top of the nail bed 48 and bottom of the nail plate 44 can reach a level at which the unwanted organism can be deactivated without causing substantial unwanted injury or substantial permanent injury to surrounding tissue.

Figure 7:
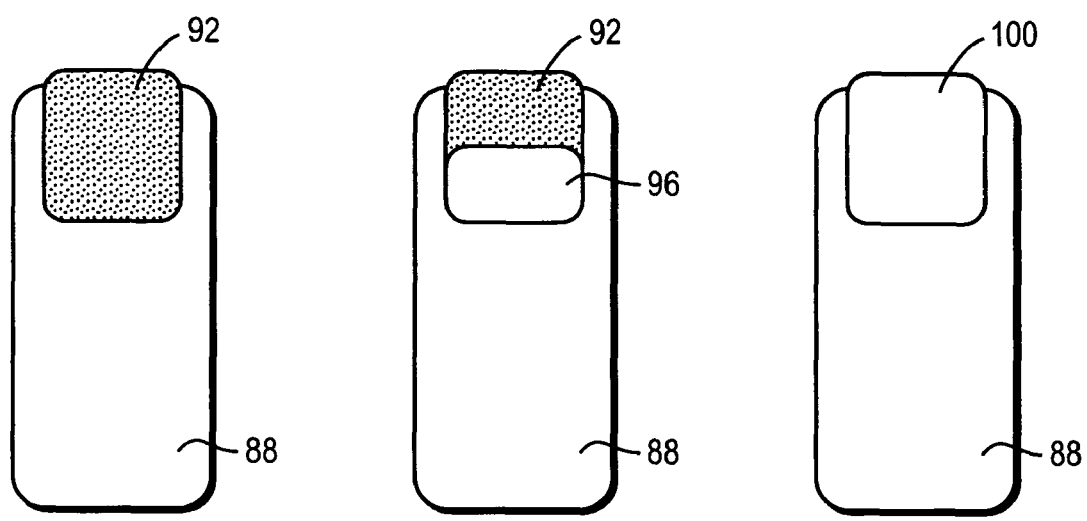
FIG. 7 depicts an exemplary mechanism for improving the appearance of a diseased nail according to the invention.

FIG. 7 shows an exemplary mechanism for improving the appearance of a diseased nail. An appendage 88 (e.g., a finger or a toe) includes a nail having a diseased portion 92 affected by an unwanted organism. After a single treatment or after series of treatments, at least a portion of the unwanted organism can be deactivated, and healthy nail 96 can push the diseased portion 92 out as the nail grows out. If the unwanted organism is substantially deactivated such that the disease state can not reoccur, the nail eventually can return to a substantially healthy state 100 free of disease. The diseased portion 92 can be cut or scraped as the nail grows out to facilitate removal of the diseased portion and/or the unwanted organism.

Figure 8:
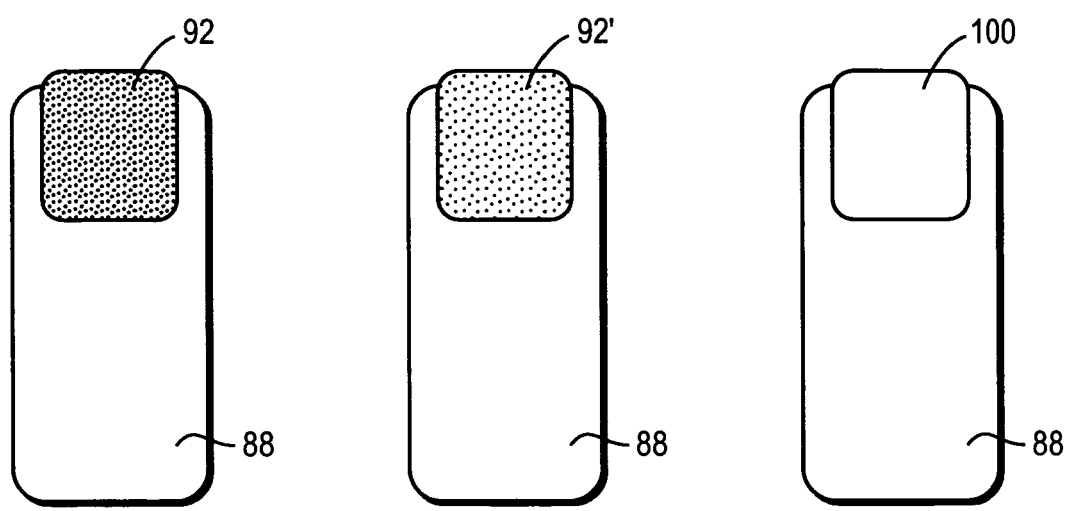
FIG. 8 depicts another exemplary mechanism for improving the appearance of a diseased nail according to the invention.

FIG. 8 shows another exemplary mechanism for improving the appearance of a diseased nail. The appendage 88 (e.g., a finger or a toe) includes a nail having the diseased portion 92 affected by an unwanted organism. After a single treatment or after series of treatments, at least a portion of the unwanted organism can be deactivated, and the discoloration of the diseased portion 92' can lighten. If the unwanted organism is substantially deactivated such that the disease state can not reoccur, new nail growth can return the nail to a substantially healthy state 100 free of disease. The diseased portion 92 or 92' can be cut or scraped as the nail grows out to facilitate removal of the diseased portion and/or the unwanted organism.

In one embodiment, one or more holes can be drilled into the nail plate 44 prior to delivering the beam of radiation 68. A hole can facilitate delivery of the beam of radiation to the nail bed 48 by removing an unwanted absorber such as the nail plate 44 or the disease itself. A hole also can facilitate delivery of a dying agent or a chromophore to the nail plate 44 or the nail bed 48, can allow heat to diffuse from the nail bed 48 during a treatment, and can facilitate cooling of the nail plate 44 by increasing nail surface to air contact.

In one embodiment, the predetermined wavelength can be selected by obtaining a sample of a diseased nail (e.g., a nail scraping or clipping) and examining the sample, or a culture grown from the sample, under a microscope to determine the source of the disease. In one embodiment, a spectroscopic measurement of the diseased nail is made to determine the absorption spectrum of the cultured organism. Once the unwanted organism is identified, a wavelength corresponding to an absorption peak for that organism can be selected. For example, if the source of the infection is a bacterium that absorbs light having a wavelength in a range of about 500 nm to about 600 nm, a light source having a suitable wavelength can be used to eliminate the bacterium. In addition, the wavelength region can be selected by avoiding a region where healthy tissue surrounding the diseased nail has a strong absorption feature. In one detailed embodiment, a wavelength is selected where the cultured organism shows a strong absorption feature and where healthy tissue surrounding the diseased nail shows a weak absorption feature.

In one embodiment, the method of selecting a predetermined wavelength is based on treating one or more of the typical sources of infection. For example, three of the most common fungi (e.g., dermatophytes) that cause nail disease are epidermophyton floccosum, trichophyton rubrum, and trichophyton metagrophytes. Each of these dermatophytes are orange to brown in color. For example, when grown in a Petri dish, epidermophyton floccosum colonies are a brownish-orange on the bottom of the colony and a brownish-yellow on the top of the colony; trichophyton rubrum is blood red at the bottom of the colony and a whitish-cream on the top of the colony; and trichophyton mentagrophytes is a pale pinkish brown on the bottom of the colony and cream on the top of the colony. As a result of the orange/red/brown color of the dermatophytes responsible for the nail disease, a blue to green wavelength (e.g., about 400 nm to about 550 nm) can be selected. In some embodiments, especially embodiments in which the source of the infection has a reddish color, the wavelength selected can be within the blue to orange region (e.g., about 400 nm to about 600 nm). In certain embodiments in which injury to the nail bed 48 and/or surrounding tissue is a concern, wavelengths that are absorbed by blood can be avoided. For example, wavelengths between about 500 nm and about 600 nm can be avoided. In some embodiments, the wavelength that is best absorbed by the organism can be between about 500 nm and about 750 nm, between about 600 nm and about 700 nm, or between about 530 nm and about 600 nm.

In one embodiment, the method of selecting a predetermined wavelength can be based on using water as an absorber. A wavelength well absorbed by water, but not well absorbed by the nail plate 44 can permit radiation to pass through the nail plate 44 and deposit energy in a top portion of the nail bed 48. For example, a wavelength in the near to mid-infrared region can be used (e.g., about 1,400 nm, about 1,450 nm, or about 1,900 nm).

In some embodiments, the energy source includes a radiofrequency (RF) generator. RF energy can be used to produce heat within a diseased nail to deactivate the disease causing organisms. In general, tissue is resistively heated by RF energy. Healthy nail tissue, however, is formed of an insulating material, and RF energy, therefore, is not strongly absorbed. In a diseased nail, the organism causing the disease can be conductive, and provide enough conductivity to absorb the RF energy. As a result, RF energy directed to a target area of a diseased nail can preferentially heat the organism. An RF delivery system can be capacitively coupled to the nail to facilitate delivery of the RF energy. One technique to capacitively couple the RF delivery system to the nail plate includes placing a broad area probe (e.g., a broad area electrode) over a large portion of the nail plate of the diseased nail. A radiofrequency is applied that can provide sufficient current to treat the diseased nail. In some embodiments, the frequency used is greater than the frequency typically used by electrocautery devices used for heating tissue. For example, in one embodiment, the frequency used to treat the diseased nail is greater than about 50 MHz.

In some embodiments, the energy source includes a microwave generator. The microwave energy can be used to thermally deactivate the unwanted organism without causing unwanted side effects to the patient or substantial injury to the tissue surrounding the diseased nail. In general, the beam of microwave energy can excite water molecules in the nail bed without substantially being absorbed by the nail plate.

In some embodiments, the energy source includes an ultrasound generator, which can be, for example, a high intensity ultrasound source or a high power focused ultrasound source. The ultrasonic energy can be used to thermally deactivate the unwanted organism without causing unwanted side effects to the patient or substantial unwanted or permanent injury to the tissue surrounding the diseased nail. Due to the large impedance mismatch of sound waves between a patient's relatively hard nail plate and soft nail bed tissue, ultrasonic energy devices are particularly well suited to provide selective energy deposition. As a result, ultrasonic energy devices can deliver sufficient energy to deactivate the source of the infection, while not causing substantial unwanted injury to surrounding tissue.

For example, ultrasonic energy directed to a diseased nail can be substantially reflected at the junction between the nail plate and the nail bed. As a result, the nail bed will not be as strongly heated as the nail plate by the ultrasound energy. Moreover, in general, the nail plate has a higher attenuation or absorption than the underlying nail bed. Thus, a high intensity, focused ultrasound device applied to the nail plate via a broad area probe placed over the surface of the diseased nail effectively heats up the nail plate without causing excessive thermal damage to the underlying nail bed.

In various embodiments, the pulsewidth can be selected to limit exposure and thermal damage to tissue surrounding the diseased nail. In one embodiment, the pulsewidth used is determined by the average size of the infecting organism. For example, the average particle size of the organism can be determined prior to delivering radiation to the diseased nail. In one embodiment, the size of the organism can be determined by collecting a diseased nail scraping or clipping from the patient, and examining the organism found in the scraping or clipping. The size or average size of the organism particle (s) can be measured, for example, using a microscope.

Once the average particle size is determined, a pulsewidth equal to or less than the thermal relaxation time for the organism can be used. For example, if the average particle size is about 10 μm, the pulsewidth selected can be about 0.05 ms. In general, the pulsewidth can scale as the square of the particle size. Thus, if the average particle size measured from a sample is about 100 μm, then the pulsewidth used to thermally deactivate the organism can be about 5 ms.

In some embodiments, the energy or fluence of the beam of radiation is predetermined so as to thermally destroy the particular source of the disease without causing substantial adverse side effects for the patient or substantial injury to surrounding tissue. In one embodiment, the fluence is selected after determining the source and/or size of the infection. Accordingly, the fluence can be tuned to preferentially heat the source of the disease without damaging or substantially injuring surrounding tissue.

In general, substantially all of the electromagnetic radiation within a broad wavelength range can be transmitted through a diseased nail in the early stages of infection. If an infection has progressed and the diseased nail is cloudy, yellow, or thick, a portion of the diseased nail can be scraped away, and/or an index matching solution can be applied to the diseased nail to improve its clarity. The index matching solution can be introduced to or infused in a porous region of the nail. For example, a porous nail can appear cloudy due to a difference in the index of refraction between air in the pores and the solid nail. To reduce the cloudiness and improve light transmission through the nail, the index matching solution can be applied to the nail to fill the voids, thereby decreasing the difference in the index of refraction. In general, index matching solutions are transparent fluids, such as, for example, water, glycol (e.g., ethylene glycol), glycerin, and mineral oil.

In one embodiment, an oral medication can be ingested and/or a topical ointment or cream can be applied to the diseased nail before, during, or after treatment with a beam radiation. For, example, after radiation treatment, a topical, such as, for example, potassium permanganate, ciclopirox olamine, an azole, or an organic acid can be applied to the treated nail. One or more additional rounds of the topical can be applied at a later time (e.g., the next day, the next week, or one or more months). In addition, one or more rounds of radiation treatment can be performed to the diseased nail to ensure that the source of the infection is thermally destroyed. Alternatively or in addition, a medication, such as an oral or intravenous medication, can be administered before, during, or after a schedule of radiation treatments. In some embodiments, portions of an appendage that do not require irradiation can be masked off to avoid unwanted exposure to radiation.

In one detailed embodiment, a treatment is performed using a pulsed, coherent beam of radiation having a laser fluence in the range of about 4 $J/cm^2$ to about 20 $J/cm^2$, a spotsize of about 7 mm, and a wavelength of about 595 nm. The fluence can be selected based on the thickness of the nail to be treated; for example, a thicker nail can require a higher fluence. After each pulse, the beam can be moved from the target area to a neighboring target area. The pulse rate can be about 1 pulse per second. Radiation can be applied to substantially the entire nail plate by incrementally moving the beam. After substantially all of the entire nail plate is irradiated, the treatment can be stopped, or the treatment can be repeated by going over the nail one or more additional times. Treatment can be terminated when the patient indicates a sensation of pain, after a predetermined number of cycles of treatment, or after a predetermined number of pulses of radiation.

In one exemplary embodiment, a diseased nail was treated over a three month period using a Candela V-Beam model dye laser having a wavelength of about 595 nm, a spotsize of about 10 mm, a pulse duration of about 20 ms, and a fluence of between about 3.5 $J/cm^2$ to about 4 $J/cm^2$, or using a Candela V-Beam model dye laser having a wavelength of about 595 nm, a spotsize of about 7 mm, a pulse duration of about 20 ms, and a fluence of about 8 $J/cm^2$. Each treatment consisted of moving the beam of radiation over the nail for three cycles, twice per week, for 24 total treatments. No topical medicine was applied to the nail. After one week of treatment, the diseased portion of the nail did not spread to other portions of the nail. After one month of treatment, the diseased portion of the nail had decreased in size. After two months and during the third month of treatment, respectively, the diseased portion of the nail continued to decrease in size. After three months of treatment, the nail was substantially without disease and was substantially completely healthy.

In another exemplary embodiment, a diseased nail was treated over a three month period using a Candela V-Beam model dye laser having a wavelength of about 595 nm, a spotsize of about 10 mm, a pulse duration of about 20 ms, and a fluence of between about 3.5 $J/cm^2$ to about 4 $J/cm^2$. Each treatment consisted of passing the probe over the nail a single time, twice per week, for a total of 24 treatments. After three months of treatment, the size of the diseased portion of the fingernail was reduced, and a healthy portion of the nail was growing out to the cuticle.

Figure 9B:
FIG. 9B is a photograph of the diseased fingernail shown in FIG. 9A twenty days after a treatment according to the invention.
Figure 9A:
FIG. 9A is a photograph of a patient's diseased fingernail prior to treatment.

FIG. 9A shows a diseased fingernail of a 65 year old women prior to treatment. This particular patient was in bad health and had received steroids for a month prior to beginning her treatment. As a result of her health and prior medical history, oral treatments and ointments were not an option. A culture of a nail sample indicated that the nail disease was of the hyperkeratotic form with nail matrix involvement. This patient received two to three applications (e.g., two to three cycles) of a Candela V-beam dye laser having a wavelength of about 595 nm, a spotsize of about 7 mm, a pulse duration of about 20 ms, and a fluence of about 7.5 $J/cm^2$. Twenty days after the first treatment, the patient came in for a second treatment. FIG. 9B shows the diseased nail prior to the second treatment. As shown in FIG. 9B, a healthy portion of the nail is growing out to about the region of the cuticle.

While the invention has been particularly shown and described with reference to specific illustrative embodiments, it should be understood that various changes in form and detail may be made without departing from the spirit and scope of the invention as defined by the appended claims.

What is claimed:

1. A method of treating a diseased nail having a nail bed and a nail plate comprising:
   generating optical radiation having a wavelength in excess of about 400 nm;
   generating radio-frequency energy;
   delivering through the nail plate to the nail bed the optical radiation and the radio-frequency energy in an effective amount to cause the optical radiation and the radio-frequency energy to be absorbed by the nail bed and converted to thermal energy that is trapped by the nail plate of the diseased nail; and
   thermally deactivating at least one unwanted organism without causing substantial unwanted injury to at least one of the nail bed and the nail plate.

2. The method of claim 1 further comprising delivering pulsed optical radiation through the nail plate to the nail bed.

3. The method of claim 2 further comprising moving the pulsed optical radiation after each pulse.

4. The method of claim 3 further comprising irradiating substantially all of the nail bed by moving the optical radiation.

5. The method of claim 2 further comprising delivering a second series of pulses of optical radiation after an interval of time.

6. The method of claim 5 wherein the second series of pulses irradiates substantially all of the nail bed.

7. The method of claim 1 further comprising delivering the optical radiation until occurrence of an event.

8. The method of claim 7 wherein the event includes a patient having the diseased nail indicating a sensation of pain.

9. The method of claim 7 wherein the event includes delivering a predetermined number of pulses.

10. The method of claim 1 wherein thermal deactivation comprises killing the at least one unwanted organism.

11. The method of claim 1 further comprising delivering the optical radiation at a rate of one pulse per second.

12. The method of claim 1 wherein the optical radiation and the radio-frequency energy are absorbed by a target chromophore in the nail bed in the absence of an exogenously applied chromophore or photosensitizer.

13. The method of claim 1 wherein the at least one unwanted organism comprises at least one of a bacterium, a mold, a fungus, a virus, and a parasite.

14. The method of claim 13 wherein the fungus is a dermatophyte selected from the group consisting of epidermophyton floccosum, trichophyton rubrum, and trichophyton mentagrophyte.

15. The method of claim 1 further comprising using a laser to provide the optical radiation.

16. The method of claim 15 wherein the laser comprises a pulsed dye laser.

17. The method of claim 1 wherein the optical radiation comprises a wavelength between about 400 nm and about 1,100 nm.

18. The method of claim 1 wherein the optical radiation comprises a wavelength between about 400 nm and about 1,750 nm.

19. The method of claim 1 wherein the effective amount of the optical radiation comprises a fluence exceeding about 4 $J/cm^2$.

20. The method of claim 1 wherein the optical radiation comprises a wavelength between about 585 nm and about 600 nm.

21. The method of claim 1 wherein the effective amount of the optical radiation comprises a fluence in the range of about 4 $J/cm^2$ to about 20 $J/cm^2$.

22. The method of claim 1 wherein the optical radiation has a spotsize of between about 2 mm and about 20 mm.

23. The method of claim 1 further comprising introducing an index matching solution into a porous region of the diseased nail prior to delivering the optical radiation and the radio-frequency energy.

24. The method of claim 23 wherein the index matching solution is selected from the group consisting of mineral oil, glycerin, glycol, and water.

25. The method of claim 1 wherein the optical radiation comprises a pulsewidth equal to or less than a thermal relaxation time of the at least one unwanted organism.

26. The method of claim 1 further comprising:
culturing the at least one unwanted organism from a clipping or scrapping obtained from the diseased nail;
measuring a light absorption spectrum of the at least one unwanted organism; and
delivering the optical radiation through the nail plate to the nail bed at wavelength region where the at least one unwanted organism shows a strong absorption feature.

27. The method of claim 1 further comprising inducing an immune response to at least partially deactivate the at least one unwanted organism.

28. The method of claim 1 wherein at least a portion of the optical radiation and the radio-frequency energy is absorbed by the at least one unwanted organism.

29. The method of claim 1 wherein at least one blood vessel in the nail bed absorbs the optical radiation.

30. The method of claim 1 further comprising cooling at least a portion of the nail plate before, during or after delivering the optical radiation and the radio-frequency energy.

31. The method of claim 1 further comprising delivering the optical radiation and the radio-frequency energy to a nail root or a junction of the nail bed and the nail plate.

32. The method of claim 1 further comprising delivering the optical radiation and the radio-frequency energy in the effective amount to cause a temperature of the nail bed to be raised to a level sufficient to substantially thermally deactivate the at least one unwanted organism in the diseased nail without causing substantial unwanted injury to at least one of the nail bed and the nail plate.

33. The method of claim 1 wherein thermal deactivation comprises thermal destruction of the at least one unwanted organism.

34. The method of claim 1 wherein thermal deactivation comprises denaturing or partially denaturing one or more molecules forming the at least one unwanted organism.

35. The method of claim 1 wherein the effective amount of the radio-frequency energy provides sufficient current to treat the diseased nail.

36. The method of claim 1 further comprising using a radio-frequency delivery system to deliver the radio-frequency energy through the nail plate to the nail bed.

37. The method of claim 36 wherein the radio-frequency delivery system is capacitively coupled to the nail plate.

38. An apparatus for treating a diseased nail having a nail plate and a nail bed, comprising:
a first energy source providing optical radiation having a wavelength in excess of about 400 nm;
a second energy source providing radio-frequency energy;
a system for delivering through the nail plate to the nail bed the optical radiation and radio-frequency energy in an effective amount to cause the optical radiation and the radio-frequency energy to be absorbed by the nail bed and converted to thermal energy that is trapped by the nail plate of the diseased nail, to thermally deactivate at least one unwanted organism in at least one of the nail bed and the nail plate of the diseased nail; and
a device to position an appendage having the diseased nail during treatment.

39. The apparatus of claim 38 further comprising a cooling pad to be positioned under the appendage during treatment.

* * * * *

UNITED STATES PATENT AND TRADEMARK OFFICE
CERTIFICATE OF CORRECTION

PATENT NO.         : 8,277,495 B2
APPLICATION NO.    : 11/229024
DATED              : October 2, 2012
INVENTOR(S)        : Constantinos Demetriou and James C. Hsia It is certified that error appears in the above-identified patent and that said Letters Patent is hereby corrected as shown below:

In claim 38, Column 14, Line 41, which reads "the optical radiation and radio-frequency energy in an" should read "the optical radiation and the radio-frequency energy in an"

Signed and Sealed this
Fourth Day of December, 2012

David J. Kappos
*Director of the United States Patent and Trademark Office*